United States Patent [19]

Yamada et al.

[11] Patent Number: 4,705,805

[45] Date of Patent: Nov. 10, 1987

[54] ANTITHROMBOTIC AGENT

[76] Inventors: Koji Yamada; Tamotsu Hashimoto, both of 1188 Shimotogari, Nagaizumi-cho, Sunto-gun, Shizuoka-ken; Masao Naruse, 870-51, Kamitsuchidana, Ayase-shi, Kanagawa-ken; Yo Murayama, 4-17-6, Nakazato, Minami-ku, Yokohama-shi, Kanagawa-ken; Hideki Ninno, 376, Kumizawa-cho, Totsuka-ku, Yokohama-shi, Kanagawa-ken, all of Japan

[21] Appl. No.: 16,473

[22] Filed: Feb. 17, 1987

Related U.S. Application Data

[63] Continuation of Ser. No. 776,088, Sep. 13, 1985, abandoned, which is a continuation of Ser. No. 660,558, Oct. 15, 1984, abandoned, which is a continuation of Ser. No. 563,536, Dec. 20, 1983, abandoned, which is a continuation of Ser. No. 307,181, Sep. 30, 1981, abandoned, which is a continuation of Ser. No. 48,518, Jun. 14, 1979, abandoned.

[30] Foreign Application Priority Data

Jun. 16, 1978 [JP]  Japan .................................. 53-72965
Dec. 15, 1978 [JP]  Japan ................................. 53-154114

[51] Int. Cl.$^4$ ..................... A61K 31/22; C07C 149/00
[52] U.S. Cl. .................................... 514/548; 514/228; 514/255; 514/316; 514/331; 514/616; 544/85; 544/121; 544/130; 544/159; 544/357; 544/360; 544/391; 546/190; 546/205; 546/233; 560/251; 564/154

[58] Field of Search ................ 560/251; 514/228, 255, 514/316, 331, 548, 616; 564/154

[56] References Cited

U.S. PATENT DOCUMENTS

| | | | |
|---|---|---|---|
| 3,227,715 | 1/1966 | Bub ................................... | 564/154 X |
| 3,574,858 | 4/1971 | Volpp .............................. | 564/154 X |
| 3,663,616 | 5/1972 | Grivas et al. ....................... | 564/154 |
| 3,736,280 | 5/1973 | Grivas ................................. | 424/324 |

FOREIGN PATENT DOCUMENTS 1960027  6/1971  Fed. Rep. of Germany .
2175032 10/1973  France .

OTHER PUBLICATIONS

Ponci, et al., Chem. Abst. 69, No. 27322t (1967).
Watanabe, et al., Chem. Abst. 87, No. 5660w.
Gialdi, et al., Chem. Abst. 54, No. 6623f (1959).
Montanari, et al., Chem. Abst. 87, No. 128031z.
Ohsawa, et al., Chem. Abst. 86, No. 122891n (1976).
Gialdi, et al., Chem. Abst. 60, No. 512h.
Stetsyuk, Chem. Abst. 86, No. 133436u (1976).
Takahi, et al., Chem. Abst. 91, No. 74559c (1978).
Boshagen, Chemische Berichte, pp. 2566-2571 (1966).

Primary Examiner—Richard L. Raymond
Attorney, Agent, or Firm—Fitzpatrick, Cella, Harper & Scinto

[57]  ABSTRACT

Certain 2,2'-dithiobis-N-substituted or unsubstituted benzamides or derivatives thereof are useful as antithrombotic agents because of their ability to suppress aggregation of blood platelets.

20 Claims, No Drawings

ANTITHROMBOTIC AGENT

This application is a continuation of application Ser. No. 776,088 filed Sept. 13, 1985 (now abandoned) which is a continuation of application Ser. No. 660,558, filed Oct. 15, 1984 (now abandoned) which is a continuation of application Ser. No. 563,536, filed Dec. 20, 1983 (now abandoned) which is a continuation of application. Ser. No. 307,181, filed Sept. 30, 1981 (now abandoned) which is a continuation of application Ser. No. 48,518, filed June 14, 1979 (now abandoned).

BACKGROUND OF THE INVENTION

The present invention relates to antithrombotic agents and more specifically to agents which inhibit blood platelet aggregation.

It is considered that cerebral apoplexy and myocardial infarction are mainly caused by thrombosis. In this regard, a thrombus formed by various reasons precedes arteriosclerosis as thrombus on the vessel wall; and when thrombus in the blood flow turns to emboli, the thus formed embolism causes blood circulation disorders. Arteriosclerosis and blood circulation disorders are considered to cause cerebral apoplexy and myocardial infarction.

Recent developments in the research of the function of blood platelets have established that the blood platelets mainly contribute to formation of the thrombus. That is, the blood platelets in the blood flow are in equilibrium state with the normal vessel walls, and causes no aggregate. However, when the blood vessels are injured, the blood platelets adhere to the collagen or the basement membrane in subintimal tissue of the blood vessels. This adhesion causes a release reaction of ADP and Serotonin from the dense body of the blood platelets. The ADP and Serotonin released from the platelets causes an aggregate reaction of the blood platelets thereselves, thus causing formation of a platelet aggregate. At the same time, released ADP and Serotonin also cause a release reaction of blood platelet factor 3; and the thus released blood platelet factor 3 accelerates Thrombin formation. As a result, the blood coagulation mechanism is accelerated by the thus formed Thrombin and a thrombus is formed.

Considering the important function of the blood platelets in the formation of thrombus as above described, drugs which inhibit the functions such as adhesion, release aggregation, etc. have been tried in the prevention of cure of thrombosis. Typical drugs which inhibit platelet aggregation are non-steroidal anti-inflammatory agents such as aspirin, indometacin, etc.; pyrasol derivatives such as sulphinpyrazone; pyrimidopyrimidine derivatives such as dipyridamole; adenosine derivatives, paraverine, etc. However, superior drugs in pharmaceutical effect and safety, are in demand.

SUMMARY OF THE INVENTION

After extensive screening, it has now been found that compounds represented by the general formula (1):

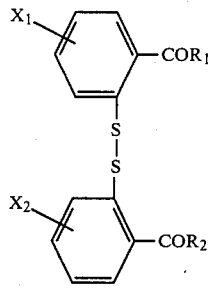

exhibit strong inhibiting activity on platelet aggregation and are of low toxicity.

More specifically, in accordance with the present invention antithrombotic agents are formulated containing a 2,2'-dithiobis-N-substituted or unsubstituted benzamide or derivative represented by the formula

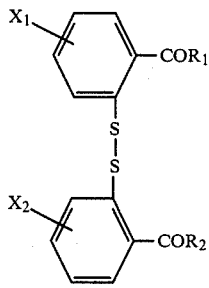

wherein $X_1$ and $X_2$ may be the same or different substituents in the same or different position but are at 3, 4, 5 or 6 position on the phenyl ring and represent a hydrogen atom, a halogen atom, a hydroxy group, a nitro group, a cyano group, an amino group, a substituted or unsubstituted lower alkyl group having 1 to 5 carbon atoms or a lower alkoxy group having 1 to 5 carbon atoms; $R_1$ and $R_2$ may be the same or different and represent an amino group, an alkylamino group having 1 to 20 carbon atoms wherein the alkyl group may be straight or branched, a dialkylamino group having 1 to 16 carbon atoms wherein the alkyl group may be straignt or branched, a substituted or unsubstituted arylamino group having 6 to 16 carbon atoms, a diarylamino group having 12 to 22 carbon atoms, a napthylamino group, an aralkylamino group having 7 to 15 carbon atoms wherein the alkyl part of the aralkyl group may be straight or branched and may be substituted by a hydroxy group, a mono-, di- or tri-hydroxyalkylamino group having 1 to 10 carbon atoms wherein the alkyl part may be straight or branched and may also be substituted, a piperidinylalkylamino group having 6 to 10 carbon atoms and wherein the alkyl part may be straight or branched and has 1 to 5 carbon atoms, an alkyloxyalkylamino group represented by the general formula (2) or a dialkyloxyalkylamino group represented by the general formula (2')

$$-NH-R_3-O-R_4-H \quad (2)$$

$$-NH-R'_3-(O-R_4-H)_2 \quad (2')$$

wherein $R_3$, $R'_3$ and $R_4$ may be the same or different and represent a straight or branched alkyl group having 1 to 5 carbon atoms, an acyloxyalkylamino group represented by the general formula (3)

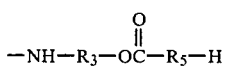
(3)

wherein $R_3$ has the same meaning as defined above and $R_5$ represents a straight or branched alkyl group having 1 to 18 carbon atoms, a hydroxyalkylaminoalkylamino group represented by the formula (4)

(4)

wherein $R_3$ has the same meaning as defined above and $R_6$ may have the same meaning as $R_3$ and represents a straight or branched alkyl group having 1 to 5 carbon atoms, an unsubstituted or hydroxy group substituted cyclohexylamino group, a morpholino group, a morpholinoalkyl group wherein the alkyl chain has 1 to 5 carbon atoms, an N'-alkylpiperazino group, a substituted or unsubstituted N'-arylpiperazino group having 10 to 15 carbon atoms, a substituted or unsubstituted aralkylpiperazino group having 11 to 20 carbon atoms wherein the alkyl chain of the aralkyl group may be substituted by an alkyloxy group having 1 to 5 carbon atoms, or a substituted or unsubstituted N'-aralkenylpiperazino group having 2 to 16 carbon atoms or a straight or branched dialkylamino group having 2 to 16 carbon atoms, that is, 2,2'-dithiobis(N-substituted-benzamide) or a derivative thereof.

The present invention also pertains to novel benzamide derivatives having a strong activity of inhibiting platelet aggregation represented by the general formula (1')

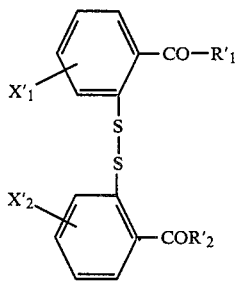

wherein, when $X'_1$ and $X'_2$ are a halogen atom, a hydroxy group, a lower alkyl group or a lower alkoxy group, $R'_1$ and $R'_2$ have the same meaning as defined above respectively and when $X'_1$ and $X'_2$ are a hydrogen atom, $R'_1$ and $R'_2$ may be the same or different and represent a dialkylamino group having 4 to 16 carbon atoms, a substituted or unsubstituted diarylamino group having 12 to 22 carbon atoms, a mono-hydroxy straight-chain alkylamino group having 1 or 4 to 10 carbon atoms, a hydroxy branched-chain alkylamino group having 3 to 10 carbon atoms, a di- or tri-hydroxyalkylamino group having 3 to 10 carbon atoms, an aralkylamino group having 7 to 15 carbon atoms wherein the alkyl part of the aralkyl group may be straight or branched and may be substituted by a hydroxy group, an alkyloxyalkylamino group represented by the general formula (2) or a dialkyloxyalkylamino group represented by the general formula (2')

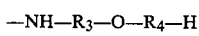
(2)

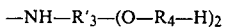
(2')

wherein $R_3$, and $R'_3$ and $R_4$ have the same meaning as defined above, an acyloxyalkylamino group represented by the general formula (3)

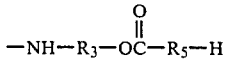
(3)

wherein $R_3$ and $R_5$ have the same meaning as defined above, a hydroxyalkylaminoalkylamino group represented by the formula (4)

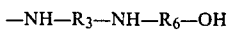
(4)

wherein $R_3$ and $R_6$ have the same meaning as defined above, a piperidinylalkylamino group having 6 to 10 carbon atoms wherein the alkyl part may be straight or branched and has 1 to 5 carbon atoms, a morpholinoalkyl group wherein the alkyl chain has 1 to 5 carbon atoms, a hydroxy substituted cyclohexyl group, an aralkenylpiperazino group, a substituted or unsubstituted arylpiperazino group or a substituted or unsubstituted N'-aralkylpiperazino group.

Included in the composition of matter aspect of the invention are the pharmaceutically acceptable nontoxic salts of the compounds defined above.

DESCRIPTION OF THE INVENTION

Antithrombotic agents of the invention as defined by the foregoing general formulae are as follows.

(1) In the general formula (1), $X_1$ and $X_2$ are a hydrogen atom and $R_1$ and $R_2$ are an amino group, an alkylamino group or a dialkyl group.
2,2'-dithiobis(benzamide)
2,2'-dithiobis(N-methylbenzamide)
2,2'-dithiobis(N-ethylbenzamide)
2,2'-dithiobis(N-propylbenzamide)
2,2'-dithiobis(N-isopropylbenzamide)
2,2'-dithiobis(N-n-butylbenzamide) (referred to as "Compound I" hereinafter)
2,2'-dithiobis(N-t-butylbenzamide)
2,2'-dithiobis(N-hexylbenzamide)
2,2'-dithiobis(N-2-ethylhexylbenzamide)
2,2'-dithiobis(N-dodecylbenzamide) (referred to as "Compound VI" hereinafter)
2,2'-dithiobis(N-octadecylbenzamide) (referred to as "Compound VII" hereinafter)
2,2'-dithiobis(N-dibutylbenzamide) (referred to as "Compound VIII" hereinafter)
2,2'-dithiobis(N-3-methyl-5-ethylhexylbenzamide)
2,2'-dithiobis{N-di-(2,3-dimethylheptyl)benzamide}

(2) In the general formula (1), $X_1$ and $X_2$ are a hydrogen atom and $R_1$ and $R_2$ are a substituted or unsubstituted arylamino, diarylamino, an aralkyl group or a napthyl group.
2,2'-dithiobis(N-phenylbenzamide) (referred to as "Compound IX" hereinafter)
2,2'-dithiobis(N-tolylbenzamide)
2,2'-dithiobis(N-p-methoxyphenylbenzamide)
2,2'-dithiobis(N-o-chlorophenylbenzamide) (referred to as "Compound X" hereinafter)
2,2'-dithiobis(N-m-chlorophenylbenzamide) (referred to as "Compound XI" hereinafter)
2,2'-dithiobis(N-p-chlorophenylbenzamide)

2,2'-dithiobis(N-p-nitrophenylbenzamide)
2,2'-dithiobis(N-o-nitrophenylbenzamide) (referred to as "Compound XII" hereinafter)
2,2'-dithiobis(N-diphenylbenzamide) (referred to as "Compound XIII" hereinafter)
2,2'-dithiobis(N-benzylbenzamide) (referred to as "Compound II" hereinafter)
2,2'-dithiobis[N-(1-methyl-3-phenylpropyl)]benzamide (referred to as "Compound XIV" hereinafter)
2,2'-dithiobis(N-2-hydroxy-2-phenylethylbenzamide) (referred to as "Compound XXXVIII" hereinafter)
2,2'-dithiobis(N-naphthylbenzamide)
2,2'-dithiobis(N-α-bromonaphthylbenzamide)
2,2'-dithiobis(N-p-cyanobenzylbenzamide)
2,2'-dithiobis(N-1,1-diphenylpropylbenzamide)
2,2'-dithiobis(N-2-methyl-2'-phenylbenzamide)
2,2'-dithiobis(N-o-acetylaminophenylbenzamide)
2,2'-dithiobis(N-naphthylbenzamide) (referred to as "Compound XXXIX" hereinafter)

(3) In the general formula (1), $X_1$ and $X_2$ are a hydrogen atom and $R_1$ and $R_2$ are a mono-, di- or tri-hydroxyalkyl group.
2,2'-dithiobis(N-hydroxymethylbenzamide) (referred to as "Compound XV" hereinafter)
2,2'-dithiobis(N-2-hydroxyethylbenzamide) (referred to as "Compound III" hereinafter)
2,2'-dithiobis(N-3-hydroxypropylbenzamide) (referred to as "Compound XVI" hereinafter)
2,2'-dithiobis(N-4-hydroxybutylbenzamide) (referred to as "Compound XVII" hereinafter)
2,2'-dithiobis(N-2-hydroxypropylbenzamide) (referred to as "Compound V" hereinafter)
2,2'-dithiobis(N-2,3-dihydroxyhexylbenzamide)
2,2'-dithiobis(N-10-hydroxydecylbenzamide)
2,2'-dithiobis(N-3-dihydroxymethylpropylbenzamide)
2,2'-dithiobis[N-3-(2-hydroxyethyl)-propylbenzamide]
2,2'-dithiobis[N-4-(2-hydroxyethyl)-butylbenzamide]
2,2'-dithiobis[N-5-(2-hydroxypropyl)-pentylbenzamide]
2,2'-dithiobis[N-3-(3-hydroxypropyl)-iso-butylbenzamide]
2,2'-dithiobis[N-2-hydroxy-1,1-di-(1'-hydroxymethyl)-ethylbenzamide] (referred to as "Compound XLI" hereinafter)

(4) In the general formula (1), $X_1$ and $X_2$ are a hydrogen atom and $R_1$ and $R_2$ are a piperidinylalkylamino group, an alkyloxyalkylamino group, an acyloxyalkylamino group, or a hydroxyalkylaminoalkylamino group.
2,2'-dithiobis(N-piperidinylmethylbenzamide) (referred to as "Compound XXXVII" hereinafter)
2,2'-dithiobis(N-piperidinylethylbenzamide)
2,2'-dithiobis(N-2-piperidinylpropylbenzamide)
2,2'-dithiobis(N-2-methyloxyethylbenzamide) (referred to as "Compound XVIII" hereinafter)
2,2'-dithiobis(N-3-ethyloxypropylbenzamide) (referred to as "Compound XXXV" hereinafter)
2,2'-dithiobis(N-4-methoxybutylbenzamide)
2,2'-dithiobis(N-5-methoxypentylbenzamide)
2,2'-dithiobis(N-6-ethoxyhexylbenzamide)
2,2'-dithiobis(N-2,2-di-methoxyethylbenzamide) (referred to as "Compound XXXIV" hereinafter)
2,2'-dithiobis(N-3,3-di-methoxypropylbenzamide)
2,2'-dithiobis(N-4,4-di-methoxybutylbenzamide)
2,2'-dithiobis(N-2,2-di-ethoxyethylbenzamide)
2,2'-dithiobis(N-4,4-di-ethoxybutylbenzamide)
2,2'-dithiobis(N-2-methoxyisobutylbenzamide)
2,2'-dithiobis(N-2-acethoxyethylbenzamide)
2,2'-dithiobis(N-3-acethoxypropylbenzamide)
2,2'-dithiobis(N-2-propionyloxybutylbenzamide)
2,2'-dithiobis(N-2-dodecanoyloxyethylbenzamide) (referred to as "Compound X'X" hereinafter)
2,2'-dithiobis(N-2-hexadecanoyloxyethylbenzamide) (referred to as "Compound XX" hereinafter)
2,2'-dithiobis(N-dodecanoyloxypropylbenzamide) (referred to as "Compound XXI" hereinafter) 2,2'-dithiobis(N-hexadecanoyloxypropylbenzamide) (referred to as "Compound XXII" hereinafter)
2,2'-dithiobis(N-2-dodecanoyloxypropylbenzamide) (referred to as "Compound XXIII" hereinafter)
2,2'-dithiobis(N-2-hexadecanoyloxypropylbenzamide) (referred to as "Compound XXIV" hereinafter)
2,2'-dithiobis[N-2-(2-hydroxyethylamino)-ethylbenzamide] (referred to as "Compound XXV" hereinafter)

(5) In the general formula (1), $X_1$ and $X_2$ are a hydrogen atom and $R_1$ and $R_2$ are a substituted or unsubstituted cyclohexylamino group, a morpholino group, or a morpholinoalkyl group.
2,2'-dithiobis(N-cyclohexylbenzamide) (referred to as "Compound XXVI" hereinafter)
2,2'-dithiobis[N-(4-hydroxycyclohexyl)benzamide] (referred to as "Compound XXXVI" hereinafter)
2,2'-dithiobis(benzmorpholide) (referred to as "Compound XXVII" hereinafter)
2,2'-dithiobis(N-morpholinomethylbenzamide)
2,2'-dithiobis(N-3-morpholinopropylbenzamide) (referred to as Compound XL" hereinafter)
2,2'-dithiobis(N-morpholinoisobutylbenzamide)

(6) In the general formula (1), $X_1$ and $X_2$ are a hydrogen atom and $R_1$ and $R_2$ are a piperadino group, an alkylpiperazino group, a substituted or unsubstituted arylpiperazino group or a substituted or unsubstituted aralkylpiperazino group or a substituted or unsubstituted aralklnylpiperazino group. 2,2'-dithiobis(N-benzpiperazide)
2,2'-dithiobis(N'-methylbenzpiperazide) (referred to as "Compound XXXII" hereinafter)
2,2'-dithiobis(N'-phenylbenzpiperazide) (referred to as "Compound XXVIII" hereinafter)
2,2'-dithiobis(N'-benzylbenzpiperazide) (referred to as "Compound IV" hereinafter)
2,2'-dithiobis(N'-diphenylmethylbenzpiperazide) (referred to as "Compound XXXIII" hereinafter)
2,2'-dithiobis[N'-(2-phenyl-2-ethyloxyethyl)benzpiperazide] (referred to as "Compound XXIX" hereinafter)
2,2'-dithiobis[N'-(3-phenyl-propene-1-yl)benzpiperazide] (referred to as "Compound XXX" hereinafter)

(7) In the general formula (1), $X_1$ and $X_2$ are a chlorine atom, a hydroxy group, a nitro group, a cyano group, an amino group, a lower alkyl group or a lower alkoxy group and $R_1$ and $R_2$ are a hydroxyamino group.
2,2'-dithiobis(5-chloro-N-2-hydroxyethyl)benzamide (referred to as "Compound XXXI" hereinafter)
2,2'-dithiobis-4-chlorobenzamide
2,2'-dithiobis(4-nitro-N-hydroxymethyl)benzamide
2,2'-dithiobis(4-amino-N-propyl)benzamide
2,2'-dithiobis(5-chloro-N-2-hydroxyethyl)benzamide
2,2'-dithiobis(6-chloro-N-2-hydroxyethyl)benzamide
2,2'-dithiobis(3-bromo-N-2-hydroxyethyl)benzamide
2,2'-dithiobis(3-fluoro-N-2-hydroxyethyl)benzamide
2,2'-dithiobis(3-amino-N-2-hydroxyethyl)benzamide
2,2'-dithiobis(5-hydroxy-N-2-hydroxyethyl)benzamide 2,2'-dithiobis(5-methyl-N-2-hydroxyethyl)benzamide
2,2'-dithiobis(5-cyano-N-phenyl)benzamide
2,2'-dithiobis(5-methoxy-N-benzyl)benzamide
2,2'-dithiobis(5-hydroxy-N-cyclohexyl)benzamide
2,2'-dithiobis(5-ethyl-N-2-butanoyloxyethyl)benzamide Suitable processes for producing the compounds set forth above are described in Japanese Patent Publication No. 41399/71; U.S. Pat. Nos. 3,736,280 and 3,663,616; Farmmaco Ed. Sci. 14, 216–239 (1959), ibid. 14, 648–665 (1959), ibid. 16, 411 (1961), Mycopathal Mycal. Appl. 24, 163 (1964). These compounds may also be produced according to the following reference examples.

On the other hand, compounds of the invention such as 2,2'-dithiobis(N'-benzylbenzpiperazide), 2,2'-dithiobis(N-hydroxymethylbenzamide), 2,2'-dithiobis(N-2-hydroxypropylbenzamide), 2,2'-dithiobis(N-3-hydroxybutylbenamide) and 2,2'-dithiobis(N-4-hydroxyhexylbenzamide) and the like are novel compounds and suitable processes for producing these compounds are described in the reference examples below.

EXAMPLE 1

Preparation of 2,2'-dithiobis(N'-benzylbenzpiperadide)-hydrochloride (Compound IV), that is, the compound represented by the general formula (1) wherein $X_1$ and $X_2$ are the same and represent a hydrogen atom, and $R_1$ and $R_2$ are the same and represent an N'-benzylpiperazino group:

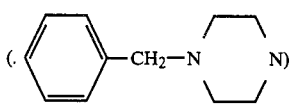

In this example, 6.9 g (0.02 mole) of 2,2'-dithio-1,1'-bis(benzoylchloride) is dispersed in 50 ml of dioxane and the mixture is cooled to 10° C. in an ice bath. To this solution, a solution of 7.0 g (0.04 mole) of benzylpiperazine dissolved in 50 ml of dioxane is added dropwise in 30 minutes. The mixture is stirred at 10° C. for one hour and then subjected to reaction with stirring at 70° C. for 2 hours. After completion of the reaction, the reaction mixture is filtered.

The filtrate is washed with acetone and recrystallized in ethanol to give 11.1 g of the desired compound as white crystals (yield 80%) having the following physicochemical properties.

(1) Elementary analysis:

|  | C | H | N | Cl | S |
|---|---|---|---|---|---|
| Found (%): | 61.30 | 5.85 | 8.15 | 9.87 | 8.97 |
| Calculated (%): (as 2HCl) | 62.14 | 5.82 | 8.05 | 10.19 | 9.22 |

(2) Melting point: above 230° C. (decomposition)

(3) IR spectrum (KBr tablet cm−1): 3400, 2950, 2550, 1639(s), 1580, 1480, 1430(s), 1290, 1260, 1150, 1040, 955, 743, 700.

(4) Solubility:

Readily soluble in water, etc. and slightly soluble in methanol, ethanol, and the like. Insoluble in ether, benzene, chloroform, and the like.

EXAMPLE 2

Preparation of 2,2'-dithiobis(N-hydroxymethylbenzamide), that is, the compound represented by the general formula (1) wherein $R_1$ and $R_2$ are the same and represent a hydroxymethylamino group ($-NH-CH_2OH$)

In this example, 3 g (0.01 mole) of 2,2'-dithio-1,1'-bis(benzamide) is dissolved in 30 ml of dimethylsulfoxide. To this mixture, 1.6 g (0.02 mole) of formalin (37% aqueous formaldehyde), is slowly added with stirring at room temperature. After completion of the addition, two drops of 1N-sodium hydroxide is added thereto and then stirring is continued at room temperature for one hour. The temperature of a water bath is raised and the reaction mixture is stirred for an additional 2 hours at 65°–70° C. in the bath. After cooling to room temperature, the reaction mixture is poured into 300 ml of cold water. The solution is allowed to stand overnight to form a white crystalline precipitate which is collected by suction filtration. The thus obtained crystaline product is washed with water three times and dried to give 3.0 g of the desired product (yield 82.5%) having the following physiocochemical properties.

(1) Melting point: 181° C. (decomposition)

(2) Elementary analysis:

|  | C | H | N | S |
|---|---|---|---|---|
| Found (%) | 52.04 | 4.66 | 7.74 | 17.20 |
| Calculated (%) | 52.72 | 4.42 | 7.68 | 17.59 |

(3) IR spectrum (KBr) tablet, cm−1): 3300, 2960(w), 1640(s), 1585, 1530(s), 1460, 1430, 1395, 1311, 1285, 1163, 1025, 750.

(4) Solubility:

Soluble in DMSO, DMF, etc., poorly soluble in ethanol, water, and the like. Insoluble in ether, benzene, chloroform and the like.

EXAMPLE 3

Preparation of 2,2'-dithiobis(N-2-hydroxypropylbenzamide), that is, the compound represented by the general formula (1) wherein $R_1$ and $R_2$ are the same and represent a 2-hydroxypropylamido group

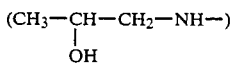

In this example, 10.3 g (0.03 mole) of 2,2'-dithio-1,1'-bis(benzoylchloride) is suspended in 50 ml of dioxane and the mixture is cooled to 10°–12° C. in an ice bath. To this solution a solution of 9.0 g (0.12 mole) of 2-hydroxypropylamine dissolved in 50 ml of dioxane is added dropwise in 60 minutes with stirring. After completion of the addition, the mixture is allowed to react at room temperature for 2 hours. After completion of the reaction, the reaction mixture is poured with stirring into 300 ml of ice water to form a white precipitate. The precipitate is filtered and dried. The thus obtained precipitate is recrystallized from 30 ml of a mixture of dioxane and water (80:20 by volume) to give 10.1 g of a white crystalline product having the following physiocochemical properties.

(1) Melting point: 175°–177° C.

(2) Elementary analysis:

|  | C | H | N | S |
|---|---|---|---|---|
| Found (%): | 57.03 | 5.51 | 6.73 | 15.11 |
| Calculated (%): | 57.11 | 5.76 | 6.66 | 15.25 |

(3) IR spectrum (KBr tablet, cm−1): 3280, 2975, 2935, 1625(s), 1586, 1580, 1430, 1305, 1140, 945, 745.

EXAMPLE 4

In this example, the same reactions are carried out as in Example 3, using the amine compounds set forth in the following Table A in place of 2-hydroxypropylamine used in Example 3 to obtain the compounds set forth in the following Table B.

TABLE A

| Exp. run. No. | Amine |
|---|---|
| 1. | 4-hydroxybutylamine |
| 2. | 3-phenyl-1-methyl-propylamine |
| 3. | diphenylamine |
| 4. | dibutylamine |
| 5. | 2-di-methoxy-ethylamine |
| 6. | 3-ethyloxy-propylamine |
| 7. | 4-hydroxy-cyclohexylamine |
| 8. | 2-hydroxy-2-phenyl-ethylamine |
| 9. | 2-hydroxy-1,1-di-(1'-hydroxymethyl)-ethylamine |
| 10. | ethanolamine |

TABLE B

| | | Physicochemical properties | | | |
|---|---|---|---|---|---|
| | | | Elementary Analysis (%) *1 | | |
| Exp. run No. | Obtained compound | m.p. (°C.) | C | H | N |
| 1 | 2,2'-dithiobis(N—4-hydroxybutylbenzamide) | 137 ~139 | 58.75 58.89 | 6.39 6.30 | 6.52 6.25 |
| 2 | 2,2'-dithiobis[N—(1-methyl-3-phenylpropyl)]benzamide | 212 ~213 | 71.49 71.78 | 6.38 6.39 | 4.78 4.93 |
| 3 | 2,2'-dithiobis(N—di-phenylbenzamide) | 203 ~205 | 74.88 74.96 | 4.75 4.65 | 4.83 4.60 |
| 4 | 2,2'-dithiobis(N—dibutylbenzamide) | 185 ~189 | 67.88 68.13 | 8.59 8.40 | 5.12 5.30 |
| 5 | 2,2'dithiobis -(N—2,2-di-methoxyethylbenzamide) | 135 ~136 | 54.92 54.97 | 6.11 5.88 | 5.88 5.83 |
| 6 | 2,2'-dithiobis(N—3-ethyloxypropylbenzamide) | 125 ~126 | 60.56 60.47 | 6.73 6.78 | 5.80 5.88 |
| 7 | 2,2'-dithiobis[N—(4-hydroxycyclohexyl)benzamide] | 234 | 62.27 62.36 | 6.73 6.45 | 5.80 5.60 |
| 8 | 2,2'-dithiobis(N—2-hydroxy-2-phenylethylbenzamide) | 214 ~217 | 65.91 65.65 | 5.18 5.25 | 5.14 5.09 |
| 9 | 2,2'-dithiobis[N—2-hydroxy-1,1-di-(1'-hydroxymethyl)-ethylbenzamide] | 126 ~128 | 51.20 51.56 | 5.19 5.47 | 5.30 5.47 |
| 10 | 2,2'-dithiobis(5-chloro-N—2-hydroxyethyl)benzamide *2 | 215 ~218 | 46.77 46.85 | 3.76 3.90 | 5.84 6.07 |

*1 Upper row: Found
*1 Lower row: Calculated
*2: 5,5'-dichloro-2,2'dithio-1,1'-bis(benzoylchloride) is used in place of 2,2'-dithio-1,1'-bis(benzochloride).

EXAMPLE 5

Preparation of 2,2'-dithiobis(N-2-dodecanoyloxyethylbenzamide) (Compound XIX), that is, the compound represented by the general formula (1) wherein $X_1$ and $X_2$ are the same and represent a hydrogen atom, $R_1$ and $R_2$ are also the same and represent N-dodecanoyloxyethylamino group

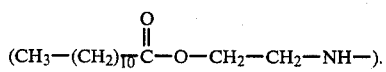

In this example, 7.9 g (0.02 mole) of 2,2'-dithio-1,1'-bis(N-2-hydroxyethylbenzamide) is dispersed in 50 ml of dioxane and the mixture is cooled to 10°–12° C. in an ice bath. To this solution, a solution of 8.8 g (0.04 mole) of dodecanoyl chloride dissolved in 50 ml of dioxane is added dropwise for 30 minutes. After completion of the addition, the mixture is allowed to react with stirring at room temperature for 2 hours. Then, the reaction mixture is poured into 300 ml of ice water to form a white precipitate. The precipitate is filtered and dried and then recrystallized from methanol to give 12.5 g of a white crystalline product having the following physicochemical properties.

(1) Melting point: 115°–118° C.
(2) Elementary analysis:

|  | C | H | N |
|---|---|---|---|
| Found (%): | 66.98 | 8.56 | 3.51 |
| Calculated (%): | 66.67 | 8.47 | 3.70 |

EXAMPLE 6

In this Example, the same reactions are carried out as in Example 5 using the benzamide compound and the chloride set forth in the following Table C in place of 2,2'-dithiobis(N-2-hydroxyalkylbenzamide) and dodecanoyl chloride to yield the compounds set forth in Table D.

TABLE C

| Exp. Run No. | used benzamide compound | used Chloride |
|---|---|---|
| 1 | 2,2'-dithiobis(N—2-hydroxyethylbenzamide) | hexdecanoyl chloride |
| 2 | 2,2'-dithiobis(N—3-hydroxypropylbenzamide) | dodecanoyl chloride |
| 3 | 2,2'-dithiobis(N—3-hydroxypropylbenzamide) | hexadecanoyl chloride |
| 4 | 2,2'-dithiobis(N—2-hydroxyethylbenzamide) | dodecanoyl chloride |
| 5 | 2,2'-dithiobis(N—2-hydroxypropylbenzamide) | hexadecanoyl chloride |

TABLE D

| Exp. run No. | Obtained compound | m.p. (°C.) | Elementary Analysis (%)* | | |
|---|---|---|---|---|---|
| | | | C | H | N |
| 1 | 2,2'-dithiobis(N—2-hexadecanoyloxyethylbenzamide) | 119 ~121 | 68.92 69.12 | 9.13 9.22 | 3.01 3.23 |
| 2 | 2,2'-dithiobis(N—3-dodecanoyloxypropylbenzamide) | 91 ~93 | 67.08 67.29 | 8.88 8.75 | 3.32 3.57 |
| 3 | 2,2'-dithiobis(N—3-hexadecanoyloxypropylbenzamide) | 101 ~103 | 69.26 69.58 | 9.36 9.45 | 2.98 3.12 |
| 4 | 2,2'-dithiobis(N—2-dodecanoyloxypropylbenzamide) | 45 | 67.01 67.29 | 8.78 8.75 | 3.64 3.57 |
| 5 | 2,2'-dithiobis(N—2-hexadecanoyloxypropylbenzamide) | 55 ~60 | 69.88 69.58 | 9.48 9.45 | 3.38 3.12 |

*Upper row: Found
*Lower row: Calculated

EXAMPLE 7

In this Example, the same reactions are carried out as in Example 1 using the amine compounds set forth in the following Table E in place of benzylpiperadine to yield the compounds set forth in the following Table F.

TABLE E

| Ex. run No. | Amine |
|---|---|
| 1 | diphenylmethylpiperazine |
| 2 | piperidinylmethylamine |
| 3 | 2-phenyl-2-ethyloxyethylpiperazine |
| 4 | 3-phenyl-propene-1-yl-piperazine |
| 5 | phenylpiperazine |

TABLE F

| Exp. run No. | Obtained compound | m.p. (°C.) | Elementary Analysis (%)* | | |
|---|---|---|---|---|---|
| | | | C | H | N |
| 1 | 2,2'-dithiobis(N'—diphenylmethylbenzpiperazide) | 215 ~216 | 67.95 67.82 | 5.94 5.94 | 6.37 6.59 |
| 2 | 2,2'-dithiobis(N'—piperidinylmethylbenzamide) | >240 | 54.48 54.62 | 6.52 6.36 | 9.45 9.80 |
| 3 | 2,2'-dithiobis[N'—(2-phenyl-2-ethyloxyethyl)benzpiperazide] | 122 ~125 | 62.35 62.12 | 6.36 6.47 | 6.72 6.90 |
| 4 | 2,2'-dithiobis[N'—(3-phenylpropene-1-yl)benzpiperazide] | >230 | 54.31 54.23 | 5.76 5.94 | 7.27 7.49 |
| 5 | 2,2'-dithiobis(N'—benzylbenzpiperazide) | 120 ~122 | 61.23 61.15 | 5.15 5.45 | 8.20 8.39 |

*Upper row: Found
*Lower row: Calculated

EXAMPLE 8

In this Example, 10.3 g (0.03 mole) of 2,2'-dithio-1,1'-bis(benzoylchloride) is dispersed in 50 ml of dioxane and the mixture is cooled to 10°–12° C. in an ice bath. To this solution a solution of 8.7 g (0.06 mole) of N-(3-aminopropyl)morpholine dissolved in 50 ml of dioxane is added with stirring in about 30 minutes. After completion of the addition, the reaction mixture is allowed to react at room temperature for 2 hours. Then, the reaction mixture is poured into 300 ml of ice water and neutralized by aqueous sodium carbonate to form a crystalline precipitate. The precipitate is filtered and dried and then recrystallized from benzene to obtain 13.5 g of a white crystalline product having the following physicochemical properties.
(1) Melting point: 147°–150° C.
(2) Elementary analysis:

| | C | H | N |
|---|---|---|---|
| Found (%): | 60.51 | 7.01 | 9.85 |
| Calculated (%): | 60.19 | 6.85 | 10.03 |

EXAMPLE 9

In this Example, the same reactions are carried out as in Example 8 using 2-(2-hydroxy-ethylamino)-ethylamine in place of N-(3-aminopropyl)morpholine to yield 2,2'-dithiobis[N-2-(2-hydroxyethylamino)-ethylbenzamide] having the following physicochemical properties.
(1) Melting point: 181°–183° C.
(2) Elementary analysis:

| | C | H | N |
|---|---|---|---|
| Found (%): | 54.78 | 5.08 | 11.50 |
| Calculated (%): | 55.20 | 6.33 | 11.71 |

As pharmaceutically accepted non-toxic salts of the disulfide compounds represented by the general formula (1) wherein $R_1$ and $R_2$ are the alkylpiperazine group or an aralkylpiperazino group, metal salts such as sulfates, hydrochlorides, hydrobromides, etc. and organic acid salts such as benzoates, fumarates, succinates, tartrates, citrates, etc. are appropriate.

In the following representative examples the utility of the compounds of the invention and certain specific embodiments thereof is illustrated. In these examples, the compounds are identified by the Roman numerals assigned above.

EXAMPLE 10

In this example, the inhibition of platelet aggregation in rabbit platelet rich plasma (in vitro) is tested.
(a) Method In this test, 9 vol. of blood is sampled from the carotid artery of rabbits (2 to 2.5 Kg) and placed in a silicon-coated flask containing 1 vol. of 3.8% sodium citrate. The thus obtained blood is centrifuged at 1,000 rpm for 15 minutes to obtain platelet rich plasma (referred to as "PRP" hereinafter). The aggregation of blood platelets is observed using an aggregometer (made by Bryston Co.) and the degree of aggregation after the addition of aggregation promoting substances is measured by nephelometry, i.e., through increase in light transmission.

The PRP (0.9 ml) is placed in a silicon-coated cuvett of the aggregometer. Then, 0.05 ml of physiological saline solution containing various concentrations of test reagents or control reagents is added and the mixture is allowed to stand for one minute. Compounds promoting aggregation are then added and the absorbancy of the solution is measured and the percent inhibition of aggregation is calculated according to the following equation:

$$\text{Percent inhibition} = \frac{C - D}{C} \times 100$$

C: Transmittancy showing the maximum percent aggregation by physiological saline solution D: Transmittancy showing the maximum percent aggregation by sample (b) Result Test for the inhibition of platelet aggregation induced by ADP, collagen and thrombin.

Addition of ADP, ($10^{-5}$M) to PRP shows an immediate transitory reduction of transmittancy based on the structural change of blood platelets and clear aggregation.

Addition of collagen to PRP shows aggregation after 1 to 2 minutes of a latent period.

Addition of thrombin shows a clear aggregation after 30 to 40 seconds of a latent period.

The inhibitory effect of Compounds I–XLI as defined above and control compounds against induced aggregation of blood platelets is illustrated in the following Table 1. These results confirm the inhibitory effect of the compounds of the invention against blood platelet aggregation.

TABLE 1

| Compound | Concentration (μg/ml) | Reagent promoting aggregation and percentage of inhibition | | |
|---|---|---|---|---|
| | | ADP | collagen | thrombin |
| Test compound | | | | |
| I | 30 | 13.4% | 16.5% | — |
| | 100 | 46.6 | 100 | — |
| II | 100 | 2.7 | 1.2 | — |
| III | 0.3 | — | 11.0 | — |
| | 1.0 | 21.3 | 39.2 | — |
| | 3.0 | 33.4 | 88.5 | — |
| | 10.0 | 69.1 | 100 | — |
| | 30.0 | 100 | — | — |
| IV | 3.0 | 28.0 | 7.6 | 31 |
| | 10.0 | 44.7 | 46.5 | 58 |
| | 30.0 | 83.3 | 100 | 84 |
| V | 1.0 | 12.5 | 25.7 | 10.0 |
| | 3.0 | 25.5 | 83.5 | 57.0 |
| | 10.0 | 54.0 | 100 | 89.6 |
| | 30.0 | 90.0 | — | 95.0 |
| VI | 30 | 0 | 0 | — |
| | 100 | 35.0 | 89.0 | — |
| VII | 30 | 0 | 0 | — |
| | 100 | 10.0 | 38.0 | — |
| VIII | 30 | 0 | 0 | — |
| | 100 | 9.0 | 13.0 | — |
| IX | 30 | 26 | 57 | — |
| X | 10 | 0 | 4 | — |
| | 30 | 24 | 63 | — |
| | 100 | 96 | 100 | — |
| XI | 10 | 0 | 0 | — |
| | 30 | 29 | 99 | — |
| | 100 | 96 | 100 | — |
| XII | 30 | 20 | 45 | — |
| | 100 | 50 | 90 | — |
| XIII | 30 | 16 | 12.2 | — |
| | 100 | 60 | 47 | — |
| XIV | 30 | 28 | 24 | — |
| XV | 3 | — | 22 | — |
| | 10 | 0 | 56 | — |
| | 30 | 46 | 100 | — |
| XVI | 1 | — | 8 | — |
| | 3 | 42 | 50 | — |
| | 10 | 64 | 78 | — |
| | 100 | 88 | 100 | — |
| XVII | 3 | — | 0 | — |
| | 10 | — | 97 | — |
| | 30 | 45 | 100 | — |
| | 100 | 100 | 100 | — |
| XVIII | 10 | — | 40 | — |
| | 30 | — | 100 | — |
| | 100 | 75 | 100 | — |
| XIX | 30 | 12 | 54 | — |
| | 100 | 72 | 100 | — |
| XX | 30 | 0 | 0 | — |
| | 100 | 23 | 33 | — |
| XXI | 30 | 5 | 0 | — |

TABLE 1-continued

| Compound | Concentration (μg/ml) | Reagent promoting aggregation and percentage of inhibition | | |
|---|---|---|---|---|
| | | ADP | collagen | thrombin |
| | 100 | 32 | 33 | — |
| XXII | 30 | 0 | 0 | — |
| | 100 | 40 | 18 | — |
| XXIII | 30 | 19 | 52 | — |
| | 100 | 93 | 100 | — |
| XXIV | 30 | 0 | 19 | — |
| | 100 | 59 | 86 | — |
| XXV | 30 | 10 | 42 | — |
| XXVI | 30 | 30 | 25 | — |
| XXVII | 1 | — | 40 | — |
| | 3 | 40 | 59 | — |
| | 10 | 60 | 100 | — |
| | 30 | 100 | 100 | — |
| XXVIII | 3 | — | 14 | — |
| | 10 | 19 | 55 | — |
| | 30 | 55 | 99 | — |
| XXIX | 3 | — | 0 | — |
| | 10 | 32 | 55 | — |
| | 30 | 43 | 100 | — |
| XXX | 30 | 17 | 40 | — |
| XXXI | 1 | — | 26 | — |
| | 3 | 0 | 100 | — |
| | 10 | 43 | 100 | — |
| | 30 | 80 | 100 | — |
| | 100 | 100 | 100 | — |
| XXXII | 1 | — | 2 | — |
| | 3 | 26 | 59 | — |
| | 10 | 62 | 90 | — |
| | 30 | 100 | 100 | — |
| XXXIII | 30 | 16 | 22 | — |
| XXXIV | 3 | 21 | 21 | — |
| | 10 | 35 | 87 | — |
| | 30 | 83 | 100 | — |
| XXXV | 10 | — | 15 | — |
| | 30 | — | 31 | — |
| | 100 | 35 | 100 | — |
| XXXVI | 10 | — | — | — |
| | 30 | — | 8 | — |
| | 100 | 35 | 95 | — |
| XXXVII | 10 | — | — | — |
| | 30 | — | — | — |
| | 100 | 20 | — | — |
| XXXVIII | 10 | — | — | — |
| | 30 | — | — | — |
| | 100 | 12 | 19 | — |
| XXXIX | 10 | — | — | — |
| | 30 | — | — | — |
| | 100 | 25 | 12 | — |
| XL | 3 | 26 | 21 | — |
| | 10 | 69 | 98 | — |
| | 30 | 100 | 100 | — |
| | 100 | — | 100 | — |
| XLI | 30 | 22 | 7 | — |
| | 100 | 71 | 96 | — |
| Control compound | | | | |
| adenosine | 100 | 39 | — | — |
| papaverine | 30 | 14 | 34 | — |
| | 100 | 99 | 100 | — |
| Aspirin | 30 | — | 20 | 21 |
| | 100 | — | 34 | 65 |
| | 300 | 0 | 48 | — |

The IC$_{50}$ values of Compounds III, IV and V on ADP ($10^{-5}$M) induced aggregation are 4.8 μg/ml, 9.8 μg/ml and 7.4 μg/ml, respectively. The IC$_{50}$ values of Compounds III and IV on collagen induced aggregation are 1.1 μg/ml and 9.8 μg/ml, respectively.

EXAMPLE 11

In this example, the promotion of dissociation of platelet aggregate induced by ADP is tested.

Addition of ADP ($10^{-5}$M, final) to 0.9 ml of PRP promotes aggregation. About 4 minutes after completion of the addition, at the maximum aggregation, physiological saline solution or test reagents set forth in the following Table 2 are added and the degree of dissociation is calculated after 5 minutes according to the following equation.

$$\text{Percent dissociation} = \frac{C - E}{C} \times 100$$

C: Maximum aggregation by ADP
E: Aggregation at 5 minutes after the addition of the reagents

TABLE 2

| Reagents | Concentration µg/ml | Percent dissociation |
| --- | --- | --- |
| Compound III | 3 | 32% |
| Compound III | 10 | 57 |
| Compound IV | 10 | 44 |
| Compound IV | 30 | 59 |
| Compound V | 3 | 65 |
| Compound V | 10 | 82 |
| Physiological saline solution | — | 24 |

EXAMPLE 12

In this example, prevention of death of mice by ADP addition (in vivo) is tested. It is shown that intravenous administration of a great amount of ADP to mice causes aggregated blood platelets to be captured in the pulmonary capillaries so that the mice die of respiratory distress.

The test is carried out according to Roba's method. [Eur. J. Pharmacol. 37, 265-274 (1976)]. Specifically, CMC solution (0.3%) and CMC suspension containing the test compound and control compounds are orally administered to mice in a ratio of 0.1 ml/10 g (body weight). After one hour, an aqueous solution of ADP (60 mg/ml) is injected into the tail vein in a volume of 0.1 ml/10 g (body weight) every 10 seconds and the mortality is calculated.

In order to check the effect by intravenous administration, physiological saline solution and physiological saline solution containing the test reagents (0.5 mg/ml) is injected into the tail vein in a volume of 0.2 ml/10 g (body weight). Ten minutes thereafter (10 mg/kg) ADP-Na is injected into the tail vein as in the oral test, and the mortality is calculated.

The results are shown in the following Table 3.

TABLE 3

| Method of administration | Reagent | dosage | Score | Mortality |
| --- | --- | --- | --- | --- |
| oral administration | Control (only CMC) | — | 7/10 | 70% |
| | Compound III | 100 mg/Kg | 2/10 | 20 |
| | Compound IV | 100 | 3/10 | 30 |
| | Aspirin | 100 | 8/10 | 80 |
| | papaverin | 100 | 6/10 | 60 |
| intravenus administration | Control (only CMC) | — | 10/10 | 100 |
| | Compound IV | 10 | 5/10 | 50 |
| | Aspirin | 10 | 7/10 | 70 |

As is evident from the foregoing Table 3, compounds of the present invention are more effective in reducing mortality than control reagents in either oral or intravenous administration. On the other hand, control reagents, i.e. Aspirin and papaverin, are ineffective.

EXAMPLE 13

In this example, the acute toxicity of compounds of the invention is determined by Behrens-Karber's method using, 5 male dd-strain for each group weighing $20 \pm 1$ g. A 0.3% CMC suspension of the test compound (concentration of the test compound: 100 mg/ml) is then orally administered to each mouse.

The results are shown in the following Table 4 wherein the mortality rate for Compound III was 0/5 at 1 g/Kg administration, 1/5 at 2 g/kg administration, 4/5 at 3 g/Kg administration, 4/5 at 4 g/Kg administration. The mortality rate for compound V was 0/5 at 2 g/Kg administration, 2/5 at 3 g/Kg administration, and 4/5 at 4 g/Kg administration.

TABLE 4

| Compound | $LD_{50}$ |
| --- | --- |
| Compound I | 0.3 g/Kg or more |
| Compound II | 0.3 g/Kg or more |
| Compound III | 2 g/Kg or more |
| Compound IV | 4 g/Kg or more |
| Compound V | 3 g/Kg or more |
| Compound VIII | 1 g/Kg or more |
| Compound X | 1 g/Kg or more |
| Compound XII | 1 g/Kg or more |
| Compound XVIII | 1 g/Kg or more |
| Compound XIX | 1 g/Kg or more |
| Compound XXV | 1 g/Kg or more |
| Compound XXVI | 1 g/Kg or more |
| Compound XXVII | 1 g/Kg or more |
| Compound XXVIII | 1 g/Kg or more |
| Compound XXIX | 1 g/Kg or more |
| Compound XXX | 1 g/Kg or more |
| Compound XXXI | 1 g/Kg or more |
| Compound XL | 1 g/kg or more |
| Compound XLI | 1 g/Kg or more |

From the results illustrated in Table 4, it will be appreciated that all of the compounds have high $LD_{50}$ values and are, therefore, safe for administration at therapeutic levels.

EXAMPLE 14

When a large amount of arachidonic acid is intravenously administrated to a mouse, blood platelet aggregates are formed and caught by the microvasculature system of the lung. As a result, the mouse expires due to dyspnea.

To examine the effect of a medicine in vivo, the medicine is orally administered to test animals and thereafter arachidonic acid is administered.

In this example, the test was carried out according to the method by Uzunova A. D. et al. [Prostaglandins 13, p. 995 (1977)] Specifically, a CMC suspension consisting of 0.3% CMC solution and a medicine (test compound and reference medicine) was orally administered to mice (male dd-strain, 22-24 g). Two hours thereafter, 50 mg/Kg of sodium arachidonate was intravenously administered to the mice. The mortality results are set forth in the following Table 5.

TABLE 5

| Medicine | Dose (mg/Kg) | Score | Mortality (%) |
| --- | --- | --- | --- |
| Control (No addition of medicine) | 0 | 15/20 | 75 |
| 2,2'-dithiobis(N—2-hydroxypropyl-benzamide) | 100 | 4/20 | 20 |
| | 50 | 4/20 | 20 |
| | 25 | 8/20 | 40 |
| 2,2'-dithiobis(N—2-hydroxyethylbenzamide (Reference medicine) | 100 | 4/20 | 40 |
| | 50 | 7/10 | 70 |

TABLE 5-continued

| Medicine | Dose (mg/Kg) | Score | Mortality (%) |
|---|---|---|---|
| Aspirin (Reference Medicine) | 25 | 1/10 | 10 |
| | 12.5 | 5/10 | 50 |

As is evident from the foregoing Table 5, compounds of the invention have a good effect upon disorders involving dyspnea.

EXAMPLE 15

In this example, the same procedures are repeated as in Example 10 except that human platelet rich plasma is used in place of rabbit platelet rich plasma.

The results are shown in the following Table 6.

TABLE 6

| Compound | | Concentration (μg/ml) | Reagent promoting aggregation and the percentage inhibition | |
|---|---|---|---|---|
| | | | ADP | collagen |
| Test compound | III | 10 | 15 | 20 |
| | | 30 | 43 | 66 |
| | | 100 | 98 | 100 |
| | IV | 10 | — | — |
| | | 30 | 0 | 12 |
| | | 100 | 58 | 75 |
| | V | 3 | 47 | 13 |
| | | 10 | 61 | 39 |
| | | 30 | 81 | 100 |
| | IX | 10 | — | — |
| | | 30 | — | 5 |
| | | 100 | 25 | 56 |
| | XV | 10 | 5 | 29 |
| | | 30 | 45 | 68 |
| | | 100 | 90 | 100 |
| | XVIII | 10 | — | 10 |
| | | 30 | 20 | 45 |
| | | 100 | 65 | 100 |
| | XIX | 10 | — | — |
| | | 30 | 5 | 16 |
| | | 100 | 35 | 46 |
| | XXV | 10 | — | — |
| | | 30 | — | 4 |
| | | 100 | 10 | 25 |
| | XXVII | 10 | — | 0 |
| | | 30 | 5 | 35 |
| | | 100 | 45 | 100 |
| | XXXI | 10 | 10 | 12 |
| | | 30 | 50 | 60 |
| | | 100 | 88 | 100 |
| | XXXII | 10 | — | — |
| | | 30 | 15 | 34 |
| | | 100 | 60 | 100 |
| | XL | 10 | 65 | 40 |
| | | 30 | 85 | 100 |
| | | 100 | 100 | 100 |
| Control compound | Aspirin | 30 | 7 | 48 |
| | | 100 | 20 | 86 |

Those skilled in the art will appreciate from the foregoing that the compounds of the invention effectively prevent or supress aggregation of blood platelets in animals and humans. Such compounds are, therefore, useful as antithrombotic agents in suitable pharmaceutical formulations.

Compounds represented by the general formula (1) may be used in form of tablets, powders, capsules, injections, and the like according to usual formulation methods.

The compounds may be formulated using the usual excipients, disintegrators, binders, lubricants, pigments, vehicles, diluents, and the like as is well known in the pharmaceutical industry. For example, glucose, lactose, etc. may be used as excipients; starch, sodium alginate, etc. as disintegrators; magnesium stearate, liquid paraffin, talc, etc. as a lubricant; and syrupus simplex, ethanol, gelatine, etc. as binders. As a vehicle, methylcellulose, ethylcellulose, etc. are used as dispersing agents and glycerol, starch, etc. as plasticizers. Moreover, crystalline cellulose may preferably be used as it has the properties of a disintegrator, lubricant, binder and excipient.

Administration of the compounds represented by the general formula (1) is carried out orally or by injection. The compounds having high $LD_{50}$ values, are safe for administration in fairly high dosage levels. Minimum effective dose is about 10–500 mg/human adult, one run.

EXAMPLE 16

In this example, a tableted form of the invention is prepared by thoroughly mixing the following components in a mixing device.

| | |
|---|---|
| Compound IV | 2000 g |
| Lactose | 100 g |
| Starch | 150 g |
| Carboxymethylcellulose.Calcium (CMC—Ca) | 150 g |
| | 2400 g |

To the thus obtained powder a kneading liquid containing 100 g polyvinyl alcohol (PVA) is added. The mixture is then granulated by a known wet granulating method, dried and selected. Then, 25 g magnesium stearate is added to the granules and mixed. The material is then passed through a rotary tablet press with a pestle having a diameter of 9 mm to prepare tablets having a diameter of 9 mm, a thickness of 4 mm and a weight of 252.5 mg, each having a dosage strength of 200 mg.

EXAMPLE 17

In this example, a film coated tablet is prepared by dissolving the following vehicle components in a mixed solvent (of acetone-dichloromethane (1:1 by volume)):

Hydroxypropylmethylcellulose: 48 g
Polyethylene glycol-4000: 10 g
Titanium oxide ($TiO_2$): 30 g The liquid is then coated on the tablets obtained in Example 1 by a standard method.

EXAMPLE 18

In this example, an injectable form of the invention is prepared by adding distilled water to 500 mg of Compound IV and 50 g of glucose to make 1 L. of a solution. The solution is filtered under pressure (0.5 Kg/cm$^2$) using a membrane filter having a 0.22μ pore size (Millipore Company, FGLD 14200) and $N_2$ gas. Portions of the filtrate are then poured into 20 ml-white ampules and sealed under standard practices.

EXAMPLE 19

In this example, the same procedures are repeated as in Examples 16 and 17 except that 2,2'-dithiobis(N-2-hydroxypropylbenzamide) is used in place of Compound (IV), i.e. 2,2'-dithiobis(N-benzylpiperadinobenzamide) to prepare similar tablets.

What is claimed is:

1. A composition of matter of the formula

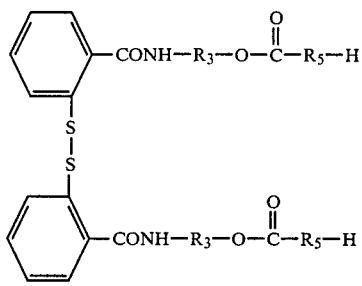

wherein $R_3$ represents a straight or branched alkylene group having 1 to 5 carbon atoms and $R_5$ represents a straight or branched alkylene group having 1 to 18 carbon atoms.

2. A composition of matter of the formula

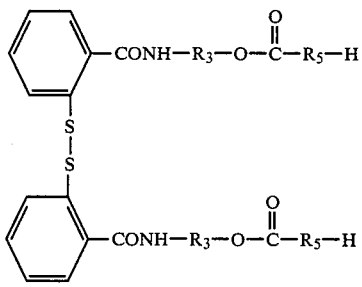

wherein $R_3$ represents an alkylene chain which is selected from an ethylene-chain, an n-propylene-chain and an isopropylene-chain and $R_5$ represents an alkylene chain which is selected from a pentadecamethylene-chain and a dodecamethylene-chain.

3. The compound according to claim 2, wherein $R_3$ represents an ethylene-chain and $R_5$ represents a pentadodecamethylene-chain, that is, 2,2'-dithiobis(N-2-hexadecanoyloxyethylbenzamide).

4. The compound according to claim 2, wherein $R_3$ represents an ethylene-chain and $R_5$ represents an undecamethylene-chain, that is, 2,2'-dithiobis(N-2-dodecanoyloxyethylbenzamide).

5. The compound according to claim 2, wherein $R_3$ represents a propylene-chain and $R_5$ represents a pentadodecamethylene-chain, that is, 2,2'-dithiobis(N-hexadecanoyloxypropylbenzamide).

6. The compound according to claim 2, wherein $R_3$ represents a propylene-chain and $R_5$ represents an undecamethylene-chain, that is, 2,2'-dithiobis(N-dodecanoyloxypropylbenzamide).

7. The compound according to claim 2, wherein $R_3$ represents an isopropylene-chain and $R_5$ represents a pentadodecamethylene-chain, that is, 2,2'-dithiobis(N-2-hexadecanoyloxypropylbenzamide).

8. The compound according to claim 2, wherein $R_3$ represents an isopropylene-chain and $R_5$ represents an undecamethylene-chain, that is, 2,2'-dithiobis(N-2-dodecanoyloxypropylbenzamide).

9. 2,2'-dithiobis(N-2-hydroxypropylbenzamide).

10. An antithrombotic pharmaceutical composition in a form for administration orally or by injection which comprises an effective antithrombotic amount of a compound represented by the formula

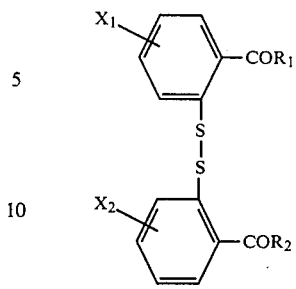

wherein $X_1$ and $X_2$ are hydrogen; $R_1$ and $R_2$ represent an acyloxyalkylamino group represented by the formula

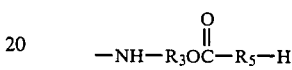

wherein $R_3$ represents a straight or branched alkylene group having 1 to 5 carbon atoms and $R_5$ represents a straight or branched alkylene group having 1 to 18 carbon atoms; or a pharmaceutically acceptable salt thereof and at least one compound for formulation selected from the group consisting of pharmaceutically acceptable excipients, disintegrators, binders, lubricants, pigments, vehicles and diluents.

11. An antithrombotic pharmaceutical composition, comprising an effective antithrombotic amount of 2,2'-dithiobis(N-2-hydroxypropylbenzamide) and a pharmacologically acceptable carrier.

12. An antithrombotic pharmaceutical composition in a form for administration orally or by injection which comprises an effective antithrombotic amount of a compound represented by formula

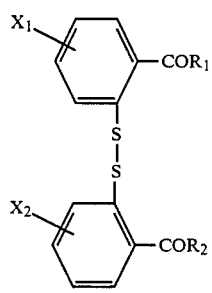

wherein $X_1$ and $X_2$ are hydrogen; $R_1$ and $R_2$ represent an acyloxyalkylamino group represented by the formula

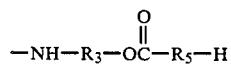

wherein $R_3$ represents an alkylene chain which is selected from an ethylene chain, an n-propylene chain, and an iso-propylene chain and $R_5$ represents an alkylene chain which is selected from a pentadecamethylene chain and an undecamethylene chain.

13. The composition according to claim 12, wherein $R_3$ represents an ethylene chain and $R_5$ represents a pentadecamethylene chain.

14. The composition according to claim 12, wherein $R_3$ represents an ethylene chain and $R_5$ represents an undecamethylene chain.

15. The composition according to claim 12, wherein $R_3$ represents a propylene chain and $R_5$ represents a pentadecamethylene chain.

16. The composition according to claim 12, wherein $R_3$ represents a propylene chain and $R_5$ represents an undecamethylene chain.

17. The composition according to claim 12, wherein $R_3$ represents a trimethylene chain and $R_5$ represents a pentadecamethylene chain.

18. The composition according to claim 12, wherein $R_3$ represents a trimethylene chain and $R_5$ represents an undecamethylene chain.

19. A method for suppressing blood platelet aggregation comprising:
administering a pharmacologically effective dosage of an antithrombotic pharmaceutical composition in a form for administration orally or by injection which comprises an effective antithrombotic amount of a compound represented by formula

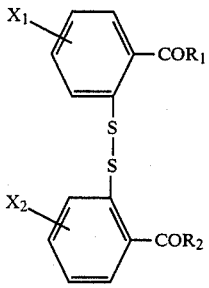

wherein $X_1$ and $X_2$ may be the same or different substituent at the 3, 4, 5 or 6 position on the phenyl ring and represent a hydrogen atom, a halogen atom, a hydroxy group, a nitro group, a cyano group, an amino group, a lower alkyl group or a lower alkoxy group; $R_1$ and $R_2$ may be the same or different and represent (1) a mono-, di- or tri-hydroxyalkylamino group having 1 to 10 carbon atoms wherein the alkyl part may be straight or branched, (2) an alkyloxyalkylamino group represented by the formula

—NH—$R_3$—O—$R_4$—H (3) a dialkyloxyalkylamino group represented by the formula

—NH—R′$_3$(O—$R_4$—H)$_2$ wherein $R_3R'_3$ and $R_4$ may be the same or different and represent a straight or branched alkylene group having 1 to 5 carbon atoms, (4) an acyloxyalkylamino group represented by the formula

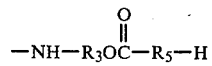

wherein $R_3$ has the same meaning as defined above and $R_5$ represents a straight or branched alkylene group having 1 to 18 carbon atoms or (5) a hydroxyalkylaminoalkylamino group represented by the formula

—NH—$R_3$—NH—$R_6$—OH wherein $R_3$ has the same meaning as defined above and $R_6$ may have the same meaning as $R_3$ and represents a straight or branched alkylene group having 1 to 5 carbon atoms, or a pharmaceutically acceptable salt thereof; and
at least one compound for formulation selected from the group consisting of pharmaceutically acceptable excipients, disintegrators, binders, lubricants, pigments, vehicles and diluents.

20. The method according to claim 19, wherein said pharmaceutically composition comprises an effective antithrombotic amount of a compound selected from the group consisting of: 2,2′-dithiobis(N-hydroxymethylbenzamide); 2,2′-dithiobis(N-2-hydroxyethylbenzamide); 2,2′-dithiobis(N-3-hydroxypropylbenzamide); 2,2′-dithiobis(N-2-hydroxypropylbenzamide); 2,2′-dithiobis (N-2-methyloxyethylbenzamide); 2,2′-dithiobis(N-3-ethyloxypropylbenzamide); 2,2′-dithiobis(N-2,2-dimethoxyethylbenzamide); 2,2′-dithiobis(N-2-hexadecanoyloxyethylbenzamide); 2,2′-dithiobis(N-2-dodecanoyloxyethylbenzamide); 2,2′-dithiobis(N-3-hexadecanoyloxypropylbenzamide); 2,2′-dithiobis(N-3-dodecanoyloxypropylbenzamide); 2,2′-dithiobis(N-2-hexadecanoyloxypropylbenzamide); and 2,2′-dithiobis(N-2-dodecanoyloxypropylbenzamide).

* * * * *

UNITED STATES PATENT AND TRADEMARK OFFICE
CERTIFICATE OF CORRECTION

PATENT NO. : 4,705,805
DATED : November 10, 1987
INVENTOR(S) : KOJI YAMADA, ET AL.

It is certified that error appears in the above-identified patent and that said Letters Patent is hereby corrected as shown below: On the title page <u>AT [76] IN THE INVENTORS</u>

"Hideki Ninno," should read --Hideki Niino,--.

<u>COLUMN 16</u>

Line 5, "dd-strain for" should read --dd-strain mice for--.

<u>COLUMN 20</u>

Line 34, "accepatable" should read --acceptable--.

<u>COLUMN 22</u>

Line 6, "$R_3R'_3$" should read --$R_3$, $R'_3$--.
Line 32, "pharmaceutically" should read --pharmaceutical--.

Signed and Sealed this

Twenty-fourth Day of May, 1988

Attest:

DONALD J. QUIGG

Attesting Officer

Commissioner of Patents and Trademarks